United States Patent
Smith et al.

(10) Patent No.: US 10,932,842 B2
(45) Date of Patent: *Mar. 2, 2021

(54) ELECTROCAUTERY HEMOSTASIS CLIP

(71) Applicant: BOSTON SCIENTIFIC SCIMED, INC., Maple Grove, MN (US)

(72) Inventors: Paul Smith, Smithfield, RI (US); Peter Dayton, Brookline, MA (US); Samuel Raybin, San Jose, CA (US); Ray H. Tong, Foxboro, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 105 days.

This patent is subject to a terminal disclaimer.

(21) Appl. No.: 16/390,745

(22) Filed: Apr. 22, 2019

(65) Prior Publication Data

US 2019/0247109 A1    Aug. 15, 2019

Related U.S. Application Data

(63) Continuation of application No. 15/352,200, filed on Nov. 15, 2016, now Pat. No. 10,307,202.

(Continued)

(51) Int. Cl.
*A61B 18/14* (2006.01)
*A61B 17/122* (2006.01)
(Continued)

(52) U.S. Cl.
CPC .......... *A61B 18/14* (2013.01); *A61B 17/1227* (2013.01); *A61B 17/1285* (2013.01);
(Continued)

(58) Field of Classification Search
CPC .............. A61B 1/1227; A61B 17/1285; A61B 18/1206; A61B 18/14; A61B 18/1442;
(Continued)

(56) References Cited

U.S. PATENT DOCUMENTS 5,853,412 A    12/1998  Mayenberger
5,916,215 A *  6/1999   Long ................... A61B 18/1487
                                                            606/41

(Continued)

FOREIGN PATENT DOCUMENTS

DE           100 11 292           9/2000

*Primary Examiner* — Michael F Peffley
(74) *Attorney, Agent, or Firm* — Fay Kaplun & Marcin, LLP

(57) ABSTRACT

A device for treating a tissue includes a capsule extending longitudinally from a proximal end to a distal end and including a channel extending therethrough, the capsule releasably coupled to a proximal portion of the device and clip arms, proximal ends of which are slidably received within the channel of the capsule so that the clip arms are movable between an open configuration, and a closed configuration. A core member is coupled to the clip alms, the core member including a proximal portion and a distal portion releasably connected to one another so that, when the core member is subjected to a predetermined load, the proximal and distal portions are separated from one another. An electrically conductive control member is connected to the core member, a proximal end of the connected member connected to a power source for delivering an electrical current to the clip arms.

13 Claims, 3 Drawing Sheets

Related U.S. Application Data

(60) Provisional application No. 62/262,729, filed on Dec. 3, 2015.

(51) Int. Cl.
 *A61B 17/128* (2006.01)
 *A61B 18/12* (2006.01)
 *A61B 17/00* (2006.01)
 *A61B 90/00* (2016.01)
 *A61B 18/00* (2006.01)

(52) U.S. Cl.
 CPC ...... *A61B 18/1206* (2013.01); *A61B 18/1442* (2013.01); *A61B 18/1447* (2013.01); *A61B 18/1492* (2013.01); *A61B 2017/00292* (2013.01); *A61B 2018/00077* (2013.01); *A61B 2018/00083* (2013.01); *A61B 2018/00136* (2013.01); *A61B 2018/00589* (2013.01); *A61B 2018/00595* (2013.01); *A61B 2018/1415* (2013.01); *A61B 2018/1475* (2013.01); *A61B 2018/1495* (2013.01); *A61B 2090/037* (2016.02)

(58) Field of Classification Search
 CPC ............ A61B 18/1447; A61B 18/1492; A61B 2018/00077; A61B 2018/00083; A61B 2018/00136; A61B 2018/00589; A61B 2018/00595; A61B 2018/1415; A61B 2018/1475; A61B 2018/1495; A61B 2090/037
 USPC .......................................................... 606/142
 See application file for complete search history.

(56) References Cited

U.S. PATENT DOCUMENTS

| | | | | |
|---|---|---|---|---|
| 6,645,205 B2 * | 11/2003 | Ginn | .................. | A61B 17/0644 128/200.24 |
| 8,162,959 B2 * | 4/2012 | Cohen | .................. | A61B 17/122 606/142 |
| 8,597,295 B2 * | 12/2013 | Kerr | .................... | A61B 18/1445 606/51 |
| 9,510,836 B2 * | 12/2016 | Zhu | ...................... | A61B 17/122 |
| 2015/0190136 A1 * | 7/2015 | Cohen | ................ | A61B 17/1227 606/143 |

* cited by examiner

ELECTROCAUTERY HEMOSTASIS CLIP

PRIORITY CLAIM

The present application is a Continuation of U.S. patent application Ser. No. 15/352,200 filed Nov. 15, 2016, now U.S. Pat. No. 10,307,202, which claims priority to U.S. Provisional Application Ser. No. 62/262,729 filed Dec. 3, 2015. The entire disclosure of the above patents/applications is expressly incorporated herein by reference.

BACKGROUND

Physicians have become more willing to perform more aggressive interventional and therapeutic endoscopic procedures including, for example, removal of larger lesions (e.g., cancerous masses), tunneling under mucosal layers in the gastro-intestinal (GI) tract to treat tissues below the mucosa, full thickness removal of tissue, inserting devices through the GI tract and then penetrating the GI organ to treat tissue outside the GI tract, and endoscopic treatment/repair of post-surgical issues (e.g., post-surgical leaks, breakdown of surgical staple lines, anastomotic leaks). These procedures may increase the risk of perforating or damaging the wall of the GI tract, or may require closure of the GI tract wall as part of the procedure. Endoscopic closure reduces cost and may reduce the trauma and inconvenience associated with these procedures. However, conventional tissue closure devices may be insufficient to close certain tissue defects.

SUMMARY

The present disclosure relates to a device for treating a tissue, comprising a capsule extending longitudinally from a proximal end to a distal end and including a channel extending therethrough, the capsule releasably coupled to a proximal portion of the device and clip anus, proximal ends of which are slidably received within the channel of the capsule. The clip arms are movable between an open configuration, in which distal ends of the clip arms extend distally past the distal end of the capsule to be separated from one another, and a closed configuration, in which the clip arms are restrained via an interior surface of the capsule so that distal ends of the clips arms are drawn toward one another. A core member is coupled to the clip arms, the core member including a proximal portion and a distal portion releasably connected to one another so that, when the core member is subjected to a predetermined load, the proximal and distal portions are separated from one another. An electrically conductive control member is connected to the core member, a proximal end of the connected member connected to a power source for delivering an electrical current to the clip arms.

In an embodiment, the proximal portion of the device may include a flexible member and a bushing at a distal end of the flexible member.

In an embodiment, the flexible member and the bushing may be separated from one another via a non-conductive element to protect the flexible member from the electrical current.

In an embodiment, the proximal and distal portions of the core member may be connected to one another via a breakable link.

In an embodiment, the capsule may be one of insulated and formed of a non-conductive material.

In an embodiment, the capsule may be formed of a conductive material.

In an embodiment, portions of the control wire may be insulated to protect a proximal portion of the device.

In an embodiment, portions of the clip arms may be insulated so that current is provided to desired portions of the clip arms.

In an embodiment, the proximal portion of the core member may include constraint tabs for engaging proximal ends of the clip arms, the distal portion including alignment protrusions for engaging corresponding cut outs extending laterally through each of the clip arms. The distal portion of the core member may be coupled to the clip arms via any means of releasable connection, such as a deformable section of either the clip arms or core member, or intermediate element fixedly connected to one of the clip arms or core member, each of which may be configured to dissociate the core member and clip arms when subject to a predetermined load.

In an embodiment, the distal ends of the clip arms may include sharp teeth extending laterally toward one another to cauterize a tissue gripped therebetween, when an electric energy is received via the clip arms.

In an embodiment, interior surfaces of the clip arms may be configured to coagulate tissue, when an electric energy is received thereby.

The present disclosure also relates to a clipping device, comprising a proximal portion and a distal portion. The proximal portion includes a flexible member extending longitudinally from a proximal end to a distal end and a bushing connected to the distal end of the flexible member. The distal portion is releasably coupled to the proximal portion so that the distal portion is deployable therefrom, the distal portion including a capsule releasably coupled to the bushing, the capsule extending longitudinally from a proximal end to a distal end and including a channel extending therethrough and clip arms extending from proximal ends slidably received within the channel of the capsule. The clip arms are movable between an open configuration, in which distal ends thereof extend distally past the distal end of the capsule to be separated from one another, and a closed configuration, in which the clip arms are restrained via an interior surface of the capsule so that the distal ends thereof are drawn toward one another. A core member is coupled to proximal ends of the clip arms, the core member including a proximal portion and a distal portion connected to one another via a breakable link designed to fail when subjected to a predetermined load. An electrically conductive control wire is connected to the core member, a proximal end of the connected member connected to a power source for delivering an electrical current to the clip arms.

In an embodiment, the device further comprises an insulating sheath extending over a portion of the control wire.

In an embodiment, the distal ends of the clip arms include sharp teeth extending laterally toward one another.

In an embodiment, portions of the clip arms may be insulated.

The present disclosure also relates to a method for treating a target tissue, comprising inserting a distal portion of a clipping device to a target area within a living body, the distal portion including a capsule and clip arms slidably received within the capsule to be movable between an open configuration, in which distal ends of the clip arms are separated from one another, and a closed configuration, in which the distal ends of the clip are drawn toward one another, the distal portion being releasably coupled to a proximal portion of the device so that the distal portion is deployable therefrom, positioning the clip arms in contact with a target tissue, and delivering an electrical energy to the clip arms via a conductive member connected to one of the capsule and the clip arms to treat the target tissue.

In an embodiment, positioning the clip arms in contact with the target tissue may include moving the clip arms toward the open configuration so that an interior surface of the clip arms are placed in contact with the target tissue to coagulate the target tissue.

In an embodiment, positioning the clip arms in contact with the target tissue may include gripping the target tissue between sharp teeth at the distal ends of the clip arms to cauterize the target tissue.

In an embodiment, the method may further comprise clipping a target portion of tissue by positioning the target portion of tissue between the distal ends of the clip arms in the open configuration and drawing the clip arms toward the closed configuration to grip the target portion of tissue.

In an embodiment, the method may further comprise locking the clip arms in the closed configuration and deploying the distal portion from the proximal portion of the device.

BRIEF DESCRIPTION

DETAILED DESCRIPTION

Figure 1:
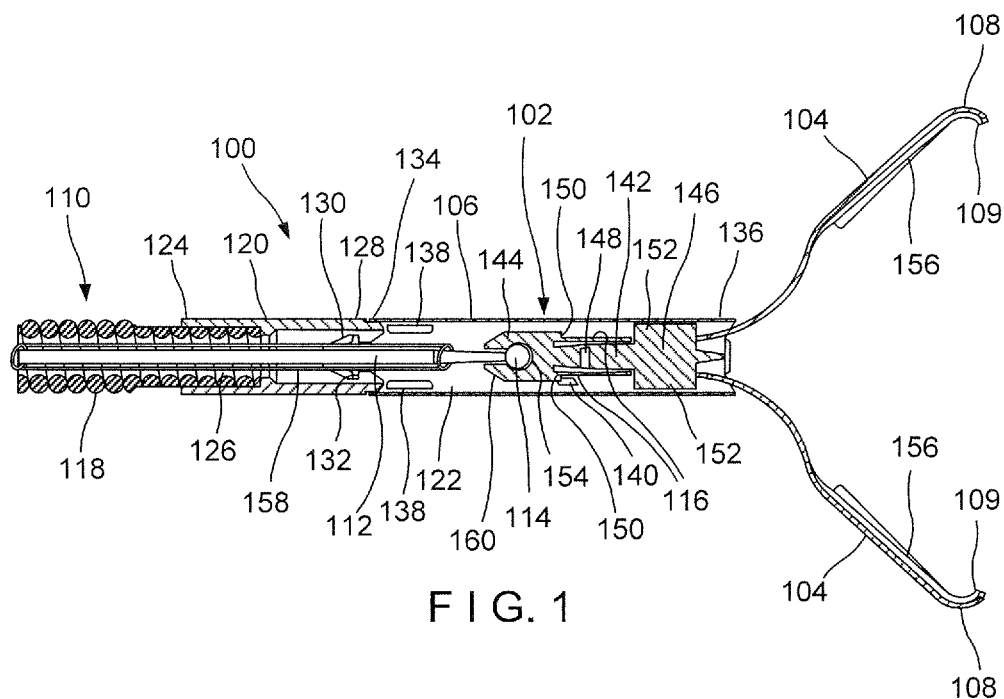
FIG. 1 shows a longitudinal cross-sectional view of a device according to an exemplary embodiment of the present disclosure.

The present disclosure may be further understood with reference to the following description and the appended drawings, wherein like elements are referred to with the same reference numerals. The present disclosure is directed to an endoscopic clipping device for treating tissue perforations, defects and/or bleeds. In particular, exemplary embodiments of the present disclosure describe a hemostatic clip having both clipping and coagulation capabilities. Portions of the clipping device may be insulated or formed of non-conductive material to achieve a desired coagulating effect. It should be noted that the terms "proximal" and "distal," as used herein, are intended to refer to a direction toward (proximal) and a direction away from (distal) a user of the device.

As shown in FIG. 1, a device 100 according to an exemplary embodiment of the present disclosure comprises a distal portion 102 insertable into a living body through, for example, a working channel of an endoscope to a target tissue to be treated. The device is sufficiently flexible to permit it to traverse a tortuous path through the body—e.g., passing through the working channel of an endoscope inserted through a natural body lumen accessed via a natural bodily orifice. The distal portion 102 includes a pair of clip arms 104 slidably received within a longitudinal channel 122 of a capsule 106. The clip arms 104 can be moved between an open configuration, in which distal ends 108 of the clip arms 104 are separated from one another to receive target tissue therebetween, and a closed configuration, in which the distal ends 108 of the clip arms 104 are moved toward one another to grip the target tissue therebetween. The distal portion 102 is releasably coupled to a proximal portion 110 of the device 100, which includes a handle (not shown) that remains outside the body accessible to a user as the distal portion 102 is deployed. The clip arms 104 are movable between the open and the closed configurations via a control member 112 extending into the capsule 106. A proximal end of the control member 112 is connected to an actuator on the handle. In this embodiment, a distal end 114 of the control member 112 is coupled to proximal ends 116 of the clip arms 104. The proximal end of the control member 112 may also be coupled to an energy source which provides electrical current through the control member 112 to the clip arms 104 to supply energy to target tissue as will be described in more detail below.

The proximal portion 110 of the device 100 includes a flexible member 118 connecting the capsule 106 to the handle. The flexible member 118 may be formed as, for example, a coil of wire or any other suitable flexible structure, which facilitates insertion of the distal portion 102 of the device 100 through even tortuous paths of the living body. The capsule 106 may be connected to the flexible member 118 via a bushing 120, which is releasably coupled to the capsule 106. The control member 112 extends through the flexible member 118, the bushing 120 and the capsule 106 to be connected to the clip arms 104. The flexible member 118 and the bushing 120 may be electrically insulated and/or formed of a non-electrically conductive material to protect the user, surrounding instruments and untargeted tissue from being affected. Insulation may be applied using powder coating, shrink tubing, or by using non-conductive components such as, for example, plastics and/or ceramics. Insulating materials may include acetal (POM), epoxy, FEP, polymide, PVDF, phenolics, PFA, polycarbonate, polysulfone, PVC, polyphenylene sulfide, polyetherimide, silicone, polyether ether ketone (PEEK), polytetrafluoroethylene (PTFE) and polyethylene. A thickness of the insulation may be between 0.0005 inches (0.0127 mm) and 0.020 inches (0.508 mm) and, more particularly, between 0.002 inches (0.0508 mm) and 0.006 inches (0.1524 mm).

The bushing 120 extends longitudinally from a proximal end 124 attached to a distal end 126 of the flexible member 118 to a bushing distal end 128 releasably coupled to the capsule 106. In one embodiment, the bushing 120 may include at least one opening 130 extending laterally therethrough for receiving a corresponding connecting tab 132 of the capsule 106. The bushing 120, however, may include a plurality of openings 130 and in one particular embodiment, includes a pair of openings 130 diametrically opposed to one another. Similarly to the capsule 106 and the flexible member 118, the bushing 120 may be insulated and/or formed of a non-conductive material to prevent surrounding areas from being affected by the electrical current passing through the control member 112, which passes therethrough. In another embodiment, a length of the control member 112 passing through the flexible member 118 and the bushing 120 may be insulated and/or covered with a sheath 158 to prevent the electrical current from passing from the control member 112 to the surrounding portions of the device 100. The insulation and/or sheath 158 covering the control member 112 may provide additional protection to the surrounding portions of the clipping device. In this embodiment, however, the flexible member 118 and the bushing 120 are not required to be insulated/non-conductive.

The capsule 106 includes a number of connecting tabs 132 corresponding to the pair of openings 130 in the bushing 120. The capsule 106 extends longitudinally from a proximal end 134 to a distal end 136 and includes the channel 122 extending longitudinally therethrough. The connecting tab (s) 132 extends radially inward from the proximal end 134 so that, when the tab 132 is received within a corresponding one of the openings 130 of the bushing 120, the capsule 106 and the bushing 120 are coupled to one another. The capsule 106 also includes a pair of windows 138 extending laterally therethrough along a proximal portion thereof. The pair of windows 138 are sized, shaped and configured to receive locking members 140 on the proximal ends 116 of clip arms 104, as will be described in further detail below. Although the device 100 is shown as coupling the bushing 120 and the capsule 106 via the opening 130 and the connecting tab 132, the bushing 120 and the capsule 106 may be coupled to one another in any of a variety of ways so long as the bushing 120 and the capsule 106 are releasably coupled to one another and releasable upon deployment of the distal portion 102 of the device 100.

The clip arms 104 of this embodiment are connected to the control member 112 via a core member 142 including a proximal portion 144 and a distal portion 146 releasably connected to one another so that, when subjected to a predetermined load, the proximal and distal portions 144, 146 separate from one another. In one embodiment, the releasable connection may be a breakable link 148 designed to separate or break when subjected to the predetermined load. The breakable link may be formed as a weld or other suitable connection so long as the connection remains in place until subjected to the predetermined load and fails when this load is applied. The core member 142 is formed of an electrically conductive material so that the electrical current passing through the control member 112 passes through the core member 142 to the clip arms 104. The distal end 114 of the control member 112 is connected to the proximal portion 144 by, for example, an enlarged distal end 114 received within a correspondingly sized and shaped cavity 154 within the proximal portion 144. Thus, as the control member 112 is moved longitudinally relative to the capsule 106, the core member 142, and thereby the clip arms 104, are moved correspondingly relative to the capsule 106.

The proximal portion 144 of this embodiment includes a pair of tabs 150, positioned on opposite sides of the proximal portion 144, for engaging the proximal ends 116 of the clip arms 104. The distal portion 146 includes alignment protrusions 152, each of which is longitudinally aligned with a corresponding one of the tabs 150, to engage a correspondingly sized and shaped cut out extending laterally through a portion of the clip arms 104. The alignment protrusions 152 maintain alignment of the clip arms 104 relative to one another. Although the core member 142 is described and shown as a unitary element having portions connected to one another via a breakable link 148, the clip arms 104 may be connected and aligned with one another via other mechanisms. For example, the core member 142 may be unitary or comprised of two or more separate elements connected to one another in various ways by separable joint as would be understood by those skilled in the art.

The clip arms 104 are biased toward the open configuration so that, when the clip arms 104 are moved distally past the distal end 136 of the capsule 106, distal ends 108 of the clip arms 104 separate from one another to the open configuration. When the clip arms 104 are drawn proximally into the capsule 106, the clip arms 104 are moved toward the closed configuration by contact with an interior surface of the capsule 106 and held in the closed position by the capsule 106. As described above, the clip arms 104 are moved between the open and closed configurations via the control member 112. The clip arms 104 are formed of an electrically conductive material so that electrical current passed through the control member 112 passes through the clip arms 104 to target tissue in contact with the clip arms 104. The clip arms 104 and the capsule 106 are configured so that the pull distance required to draw the clip arms 104 toward the closed configuration is such that a conductive portion of the control member 112, core member 142 and clip arms 104 are never drawn into any conductive portion of the flexible member 118.

Features of the clip arms 104 with small current emitting areas such as, for example, sharp edges, may be used as cauterizing or cutting edges. For example, sharp teeth 109 at distal ends 108 of the clip arms 104 may extend laterally toward one another so that when gripping tissue therebetween, the sharp teeth 109 may be used to cauterize tissue that they contact. Features with large current emitting areas such as smooth surfaces may be used for coagulation. For example, interior surfaces 156 along a length of the clip arms 104 (i.e., the surfaces of the clip arms 104 which face one another when the clip arms 104 are drawn together) may be used to provide a coagulating effect when pressed against tissue. In another example, the clip arms 104 may be moved toward the closed configuration so that the sharp teeth 109 of the distal ends 108 are joined together to form a smooth distal edge. This smooth distal edge may be used to coagulate smaller areas of tissue. In yet another example, a distal surface of the clip arms 104, in the closed configuration, may be pressed against the target tissue to coagulate the tissue. Different areas of the clip arms 104 may provide different effects on the tissue when pressed thereagainst. In this way the geometry and material construction of the tip can vary the current density acting on the tissue. Large areas such as, for example, an interior or exterior surface of the clip arms 104, provide lower current density effects for coagulation. Smaller, sharper areas such as, for example, tips or sharp teeth 109 of the clip arms 104, provide higher current density effects for cutting. Although the exemplary embodiment shows and describes all of the clip arms 104 as entirely conductive, it is also possible to insulate portions of the clip arms 104 so that only desired portions thereof are conductive. For example, it may be desired for only the distal tips of the clip arms 104 to be conductive.

As described above, the device 100 provides for cauterization/cutting, coagulation and/or clipping of target tissue, as desired or necessary to treat a target area. The cauterization and coagulation effect may be controlled via a powering on and off of the electrical power source connected to the proximal end of the control member 112. When it is desired to cauterize or coagulate the tissue, the power source may be powered on so that electrical current is passed to the clip arms 104. Once the desired cauterization and/or coagulation effect has been achieved, or when it is desired to utilize the clipping aspect of the device 100, the power source may be powered off so that the clip arms 104 may be positioned over target tissue and clipped thereto without further application of energy to the clipped tissue. Once the target tissue has been positioned between the clip arms 104, the clip arms 104 may be moved toward the closed configuration so that the distal portion 102 of the device 100 may be deployed over the target tissue, as will be described in greater detail below.

According to an exemplary method, the distal portion 102 of the device 100 may be inserted to a target area within a living body through, for example, a working channel of an endoscope. The distal portion 102 may be inserted through the working channel, in the closed configuration. Once the distal portion 102 has reached the target area, however, the clip arms 104 may be moved to the open configuration by moving the control member 112 distally relative to the capsule 106. The clip arms 104 are movable between the open and closed configuration to grip and/or contact tissue in a manner which would achieve the desired effect. For example, to provide cutting, the distal ends 108 of the clip arms 104 may be positioned about the area of tissue to be cut, in the open configuration. The clip arms 104 may be drawn toward the closed configuration so that the portion of the target area that is desired to be cut is gripped between sharp edges or teeth 109 of the distal ends 108 of the clip arms 104. The power source may be powered on so that electrical current passing through the control member 112 passes through the clip arms 104 to the distal ends 108 to cauterize/cut the gripped tissue. It may also be desired to provide coagulation to portions of tissue in the target area. In one example, the clip arms 104 may be positioned, in the open configuration, across a portion of tissue to be treated so that interior surfaces 156 contact the tissue to be treated. The clip arms 104 may be moved slightly toward the closed configuration to increase an area of contact with the tissue. In another example, the clip arms 104, in the closed configuration, may form a smooth distal edge for coagulating tissue. The smooth distal edge may be used to coagulate more targeted portions of tissue. With the power source powered on, electrical current is passed to the clip arms 104 to coagulate tissue contacted by the clip arms 104. The above-described processes may be repeated until the desired cauterization and/or coagulation effect has been achieved.

Upon completion of the desired cauterization and/or coagulation, or when it is desired to utilize the clipping aspect of the device 100, the power source may be powered off and the clip anus 104 positioned about a portion of tissue to be clipped. Once the portion of tissue to be clipped has been positioned between the clip arms 104, the clip arms 104 are moved toward the closed configuration so that the tissue is gripped therebetween. The clip arms 104 may be moved between the open and closed configurations until the desired portion of tissue is gripped. In one particular embodiment, the distal portion 102 of the device 100 may be deployed with the clip arms 104 in the closed configuration by drawing the control member 112 further proximally until a proximal end 160 of the core member 142 is moved proximally against the connecting tabs 132 of the capsule 106. The proximal force against the tabs 132 forces the tabs 132 out of the openings 130 of the hushing 120, releasing the capsule 120 from the bushing 120. Further proximal motion of the control member 112 dissociates the core member 142 so that the proximal ends 116 of the clip arms 104 are released to engage the windows 138, locking the clip arms 104 in the closed configuration. The proximal portion 144 of the core member 142 is drawn proximally out of the capsule 106, thereby separating the distal portion 102 of the device 100 from the proximal portion and deploying the device in the body.

The above-described deployment process is one example of how the distal portion of the device 100 may be deployed. The distal portion 102 may be deployed in a variety of different ways, depending on the configuration of the core member 142 and/or the coupling between the bushing 120 and the capsule 106, so long as deployment releases the capsule 106 from the bushing 120 while also locking the clip arms 104 in the closed configuration.

Figure 2:
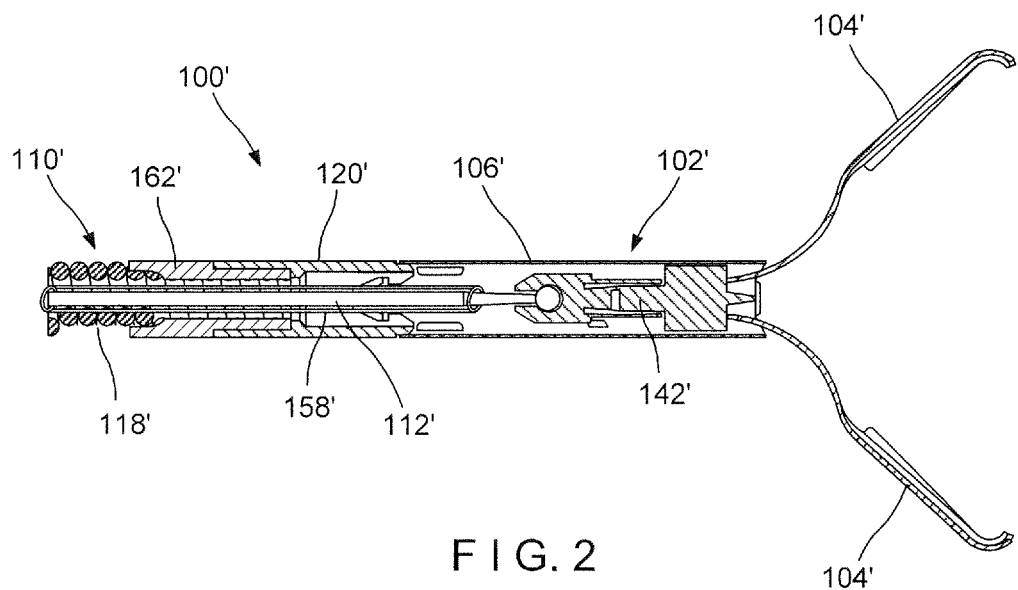
FIG. 2 shows a longitudinal cross-sectional view of a device according to an alternate embodiment of the present disclosure.

According to an alternate embodiment, as shown in FIG. 2, a device 100' is substantially similar to the device 100 described above, comprising a distal portion 102' including clip arms 104' slidably received within a capsule 106' to be moved between an open configuration and a closed configuration via a control member 112'. The device 100' is used in a manner substantially the same as the device 100. Rather than being insulated and/or formed of a non-conductive material, however, the capsule 106' is formed of a conductive material so that electrical energy may be passed thereto. For example, electrical energy may be passed through the control member 112', substantially as described above with respect to the device 100, to the capsule 106' via the core member 142' and/or clip arms 104' which come into contact with the capsule 106'.

Similarly to the device 100, the distal portion 102' is releasably coupled to a flexible member 118' of a proximal portion 110' of the device 100' via a bushing 120'. The proximal portion 110', however, further includes a non-conductive separator 162' positioned between the bushing 120' and the flexible member 118' to further protect the flexible member 118' from the electrical current. Substantially similarly to the device 100 described above, the flexible member 118' may also be protected from the electrical current by insulating portions of the control wire 112' extending therein and/or covering portions of the control wire 112' with a non-conductive sheath 158'.

Figure 3:
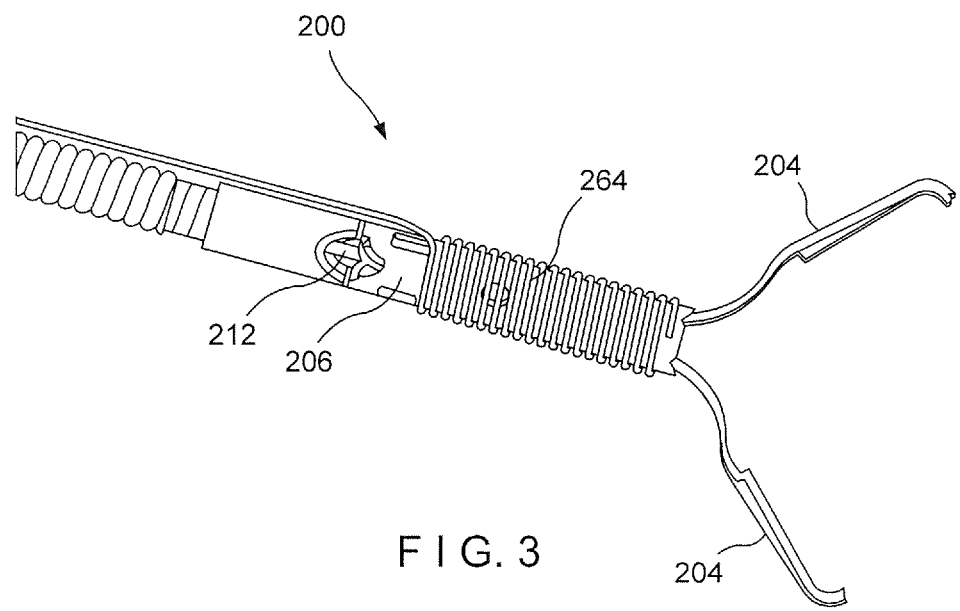
FIG. 3 shows a longitudinal side view of a device according to another exemplary embodiment of the present disclosure.
Figure 4:
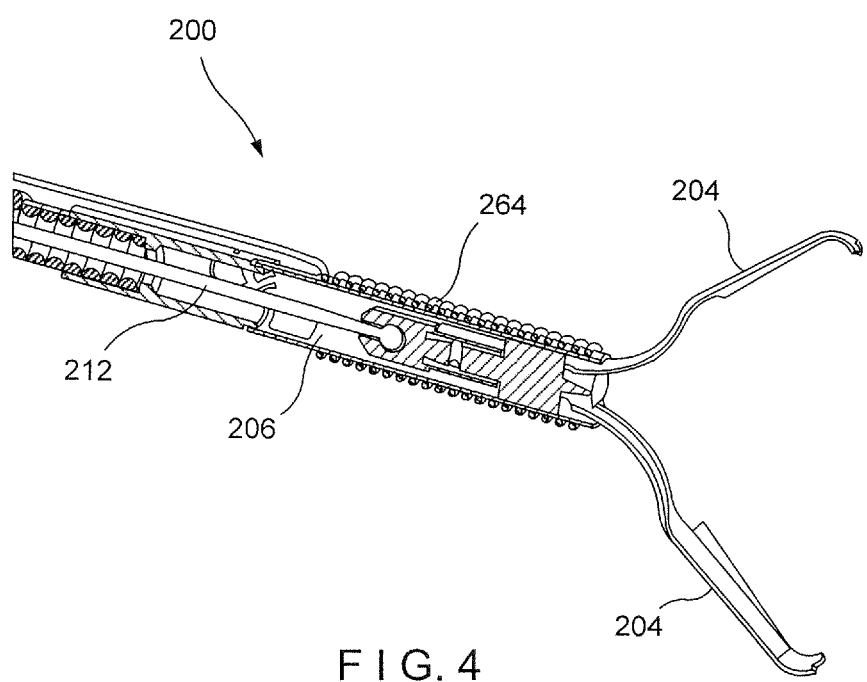
FIG. 4 shows a longitudinal cross-sectional view of the device of FIG. 3.

As shown in FIGS. 3-4, a device 200 according to another exemplary embodiment is substantially similar to the device 100, described above, comprising a pair of clip arm 204 slidable within a capsule 206 between an open configuration and a closed configuration. Rather than having an electrical current passed to the clip arms 204 via a control member 212, however, cauterization and/or coagulation via the clip arms 204 may be activated by an inductive or capacitive coupling. In particular, a conductive coil 264 may extend about an exterior surface of the capsule 206. The conductive coil 264 may be connected to a power source at a proximal end of the device 200 so that, when powered, the conductive coil 264 creates an electrical field which passes electrical energy to the clip arms 204 so that the clip alms 204 may cauterize and/or coagulate tissue in a manner substantially similar to the device 100, as described above. Since the clip arms 204 are activated by the conductive coil 264, the control member 212 is insulated and/or formed of a non-conductive material.

Figure 5:
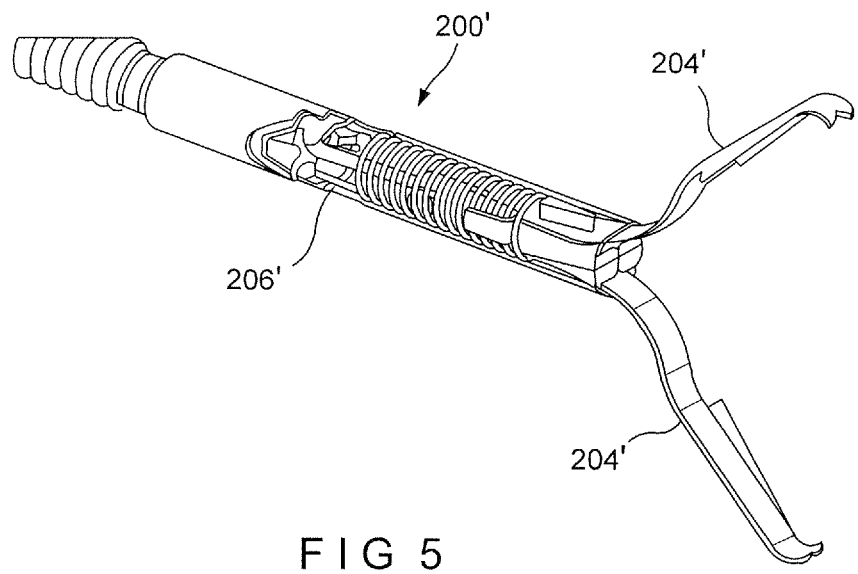
FIG. 5 shows a partially transparent perspective view of a device according to another alternate embodiment of the present disclosure.
Figure 6:
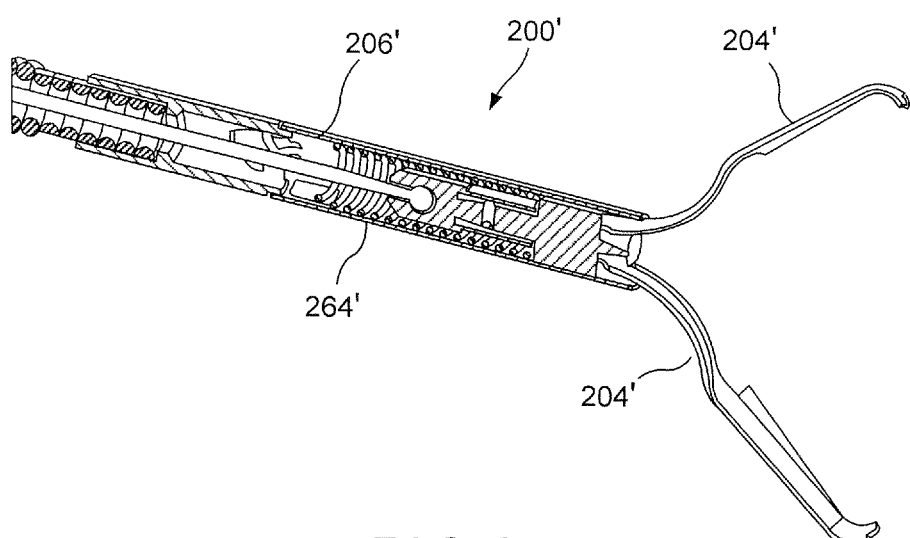
FIG. 6 shows a longitudinal cross-sectional view of the device of FIG. 5.

As shown in FIGS. 5-6, a device 200' according to an alternate embodiment is substantially similar to the device 200. Rather than a conductive coil about an exterior of a capsule, however, the device 200' comprises a conductive coil 264' extending about an interior surface of a capsule 206', the conducive coil 264' creating an electrical field for activating clip arms 204' slidably received within the capsule 206'. In another embodiment, not shown, a conductive coil may be embedded within a wall of the capsule 206'.

The devices 200, 200' may be used in a manner substantially similar to the device 100. In particular, the clip arms 204, 204' may be used to cauterize, coagulate and/or clip tissue, as described above.

Variations may be made in the structure and methodology of the present disclosure, without departing from the spirit and the scope of the disclosure. Thus, it is intended that the present disclosure cover the modifications and variations of this disclosure that may be contemplated by a person of skill in the art.

What is claimed is:

1. A device for treating a tissue, comprising:

a capsule extending longitudinally from a proximal end to a distal end and including a channel extending therethrough, the capsule releasably coupled to a proximal portion of the device;

clip arms, proximal ends of which are slidably received within the channel of the capsule so that the clip arms are movable between an open configuration, in which distal ends of the clip arms extend distally past the distal end of the capsule to be separated from one another, and a closed configuration, in which the clip arms are restrained via an interior surface of the capsule so that distal ends of the clips arms are drawn toward one another; and a conductor extending from a proximal end coupled to a source of electrical energy to a distal portion adjacent to the capsule, the conductor forming an inductive coupling with at least one of the clip arms to supply energy thereto to ablate tissue contacting the clip arms, wherein a first one of the clip arms includes a first clip arm insulated portion and a first clip arm conductive portion, a first part of the first clip arm conductive portion being configured to cauterize tissue when electrical energy is supplied to the clip while a second part of the first clip arm conductive portion is configured to coagulate tissue when electrical energy is supplied to the clip.

2. The device of claim 1, further comprising a core member coupled to the clip arms, the core member including a proximal portion and a distal portion releasably connected to one another so that, when the core member is subjected to a predetermined load, the proximal and distal portions are separated from one another.

3. The device of claim 2, wherein the proximal and distal portions of the core member are connected to one another via a breakable link.

4. The device of claim 2, wherein the proximal portion of the core member includes constraint tabs for engaging proximal ends of the clip arms, the distal portion including alignment protrusions for engaging corresponding cut outs extending laterally through each of the clip arms.

5. The device of claim 2, further comprising a control member connected to the core member, a distal end of the control member being coupled to the core member and a proximal end of the control member being connected to an actuator for moving the core member proximally and distally relative to the capsule so that the clip arms move between the open and closed configurations.

6. The device of claim 5, wherein the control member is one of electrically insulated from the clip arms and formed of a non-conductive material.

7. The device of claim 1, wherein the proximal portion of the device includes a flexible member and a bushing at a distal end of the flexible member.

8. The device of claim 1, wherein the conductor forms a coil surrounding at least proximal portions of the clip arms.

9. The device of claim 8, wherein the coil formed by the conductor extends around an exterior of at least a portion of the capsule.

10. The device of claim 8, wherein the coil formed by the conductor extends around the clip arms within the capsule.

11. The device of claim 1, wherein portions of the control member are insulated to protect a proximal portion of the device.

12. The device of claim 1, wherein the distal ends of the clip arms include sharp teeth extending laterally toward one another to cauterize a tissue gripped therebetween, when an electric energy is received via the clip arms.

13. The device of claim 1, wherein the second part of the first clip arm conductive portion is formed along an interior surface of the first clip arm.

* * * * *